United States Patent [19]
Krebber

[11] Patent Number: 6,114,409
[45] Date of Patent: *Sep. 5, 2000

[54] DENTAL MATERIAL AND TOOL FOR ITS APPLICATION

[76] Inventor: Burghardt Krebber, Schanzwiese 28, D-86899 Landsberg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/666,307

[22] PCT Filed: Jan. 4, 1995

[86] PCT No.: PCT/DE95/00007

§ 371 Date: Aug. 20, 1996

§ 102(e) Date: Aug. 20, 1996

[87] PCT Pub. No.: WO95/18597

PCT Pub. Date: Jul. 13, 1995

[30] Foreign Application Priority Data

Jan. 4, 1994 [DE] Germany .............................. 44 00 073

[51] Int. Cl.[7] .............................. C08K 7/02; A61K 6/083
[52] U.S. Cl. .................... 523/116; 523/115; 523/222; 524/494; 433/228.1
[58] Field of Search ...................... 524/494; 433/228.1; 523/115, 116, 222

[56] References Cited

U.S. PATENT DOCUMENTS

| 4,894,012 | 1/1990 | Goldberg et al. | 523/115 |
|---|---|---|---|
| 4,940,844 | 7/1990 | Blunt | 524/846 |
| 5,098,304 | 3/1992 | Scharf | 433/215 |
| 5,176,951 | 1/1993 | Rudo | 428/229 |
| 5,222,987 | 6/1993 | Jones | 523/115 |
| 5,266,609 | 11/1993 | Hall et al. | 523/116 |
| 5,387,103 | 2/1995 | Fischer | 433/89 |
| 5,512,611 | 4/1996 | Mitra | 523/116 |
| 5,548,001 | 8/1996 | Podszun et al. | 523/116 |

FOREIGN PATENT DOCUMENTS

| 3243861 C2 | 10/1985 | Germany . |
|---|---|---|
| 3 831 232 A1 | 3/1990 | Germany . |
| 3831232 A1 | 3/1990 | Germany . |
| 4219793 C1 | 10/1993 | Germany . |
| 9400070 U | 5/1994 | Germany . |
| WO 89/04640 | 6/1989 | WIPO . |

*Primary Examiner*—Andrew E. C. Merriam
*Attorney, Agent, or Firm*—Woodcock Washburn Kurtz MacKiewicz & Norris LLP

[57] ABSTRACT

Ready-to-use, packaged, dental composition curable by UV, light or laser beams, for the preparation of dental fillings, inlays, onlays, crowns, bridges, artificial teeth, dental prostheses and implantates with a container, impervious for UV or light, which houses a dental composition in such a fashion that it is affected from the effects of UV or light during storage while it can be removed for use, whereby the dental composition comprises the following: a matrix polymerizable and/or curable to a duroplastic or thermoplastic dental resin by means of UV, light or laser beams, into which a micro-fine inorganic filler is incorporated, and into which filaments or a web in the form of a mat, a ribbon, a tube or a cord is embedded; as well as a tool for applying pressure during the use of the dental composition for the purposes of filling cavities.

18 Claims, No Drawings

DENTAL MATERIAL AND TOOL FOR ITS APPLICATION

The invention relates to a dental material which is curable with UV, light or laser beams and which is useful for the preparation of dental fillings, inlays/onlays, crowns, artificial teeth, bridges, dental protheses and implantates. The invention also refers to a tool for the polymerization of the dental composition according to the invention.

Restorative dental compositions must satisfy a large number of special requirements. They must be non-poisonous and biocompatible and must lead to products which have a high tensile strength or compression strength, a high durability during use, a good esthetic appearance and an excellent resistance against chemical influences by food and saliva as well as high resistance against electro-galvanic or electro-magnetic effects.

It is widely practised to prepare dental fillings from amalgam. They are inexpensive and they have good mechanical properties. In view of the mercury content, amalgam must be considered poisonous and can create severe health hazards. Furthermore, electro-galvanic or electro-magnetic influences may be damaging to the health.

Further, gold is known as a restorative dental material. It has excellent mechanical properties. However, gold is very expensive and frequently not acceptable for esthetic reasons. In the neighborhood of other metals health problems can arise due to electrical current.

Further, ceramic materials are known which are excellently suitable for dental restorative purposes due to their good appearance and their high abrasion resistance. However, they are liable to fracture, notably if the walls are thin and they are difficult to process.

It is also known to use combinations of gold and ceramic. It is further known to use ceramic or resin blocks for milling inlays or onlays. Again, these inserts have a high risk of fracturing and the occlusion is imprecise. Further, the necessary equipment is very expensive.

Moreover, composite materials for dental restorative purposes are known, which consist of a mixture of resin, filler and dye stuff. The filler has the purpose of decreasing the tendency to shrink during polymerization and to improve certain mechanical properties. However, composite materials fracture easily.

It is further known to prepare whole artificial teeth on the basis of fiber composites (German Patent 32 43 861). These contain short carbon fibers. Such short fibers cannot sustain the high forces which are exerted across the relevant spaces or surfaces. Therefore, also this material tends to break. Also, such dental restorative products do not satisfy the above requirements. Carbon fibers are also not preferable for esthetic reasons.

U.S. Pat. No. 5,176,951 describes a process for reforcing dental prostheses. According to this process the area to be reinforced is provided with a layer of a dental material whereupon a web is layed onto this layer of material and finally a further layer of dental material is used to cover the web. According to this process a special woven web is used which must be cut with a special pair of scissors. It is not to be touched by bare hands during the application and it must be impregnated with monomer liquid prior to the application. Therefore, this process is extremely complicated in terms of skill, time and the likelyhood of failure. Above all its applications are very limited. Notably, this process is not suitable for preparing dental fillings.

It is therefore the problem of the present invention to provide a dental material which can be processed simply, quickly and without troubles and which has no limitations in terms of the scope of usefulness and which notably is also useful for dental filling purposes and which nevertheless exhibits the advantages of fiber reinforcement in an optimum way.

This problem is solved in accordance with claim 1. Further advantageous embodiments are defined in the sub-claims.

In addition to the filaments or the web microfine filler is incorporated within the matrix. By this feature, the ready-to-use material combines the advantages of having on the one side the right consistency for stable storage and on the other side the right composition for achieving the ideal combination of mechanical properties, for example, with respect to tensile strength, bending strength and impact strength as well as compression strength and the abrasion resistance.

With this measure conventional applications are decisively improved, notably with respect to the combination of impact resistance, tensile strength, compression strength and abrasion resistance. On the other side completely novel fields of application are opened up, for example, with respect to a construction of crowns having reinforcing fibers oriented in the circumferential direction whereby X-ray transparency exists. Furthermore, an X-ray transparent Maryland-bridge can be produced without any metal sub-structure. Moreover, dental fillings can be produced which are extremely stable with respect to their shape. The formation of gaps at the fringe of the material is completely prevented during and after the polymerization. The entire cavity may be filled with one single working cycle and the filling may be subsequently polymerized in one step as long as fiber material is used which has good light conduction properties. A construction layer by layer which requires so much time and is so unpleasant for the patient and costly for the dentist can be avoided. Above all, in the face of such extraordinary diversity of the fields of application, a unification of the dental material types can be achieved which has been hitherto unthinkable. With one single type dental material most varied dental operations can be executed. This has enormous advantages with respect to the training and the skills of the technicians entrusted with such a material. Therefore, the present invention constitutes a revolution in the field of resin-based dental technology.

Fiber reinforced composite materials are used whereby the fiber material may be in the form of a web or a woven material and/or filaments and especially arranged or wound. The web may preferably consist of ribbons, tubes or cords. The webs or filaments, respectively, are embedded into a matrix which consists of resins such as duroplastic resins or thermoplastic resins.

The webs are pre-impregnated with dental compositions which are in a manner known per se light- or UV- curable and/or polymerizable. Particularly suitable are compomer compositions. These matrix resins contain additionally microfine inorganic filler. Moreover, other usual inorganic or organic fillers may be used. Preferably, 5 to 80 weight-% are and especially 10 to 60 weight-% of filler may be contained in the dental composition (without the web or filaments).

The filament material may be inorganic fiber material or glass fiber material, ceramic fiber material but also organic fiber material such as polyethylene fibers, polyester fibers or the like. If a thermoplastic composition is used as the matrix, the fibers or filaments should be selected so as not to melt.

Since filaments or fibers can accept only tensile forces they should be preferably arranged in such a fashion that they are only under tensile stress. Compression forces, which are exerted onto the matrix should be reoriented in such a fashion that they exert only tensile forces onto the fibers or filaments. This is essentially achieved by orienting the webs or woven material and/or the filaments or fibers within the matrix essentially in the form of closed loops, rings and/or balls. The content of fiber material should be as high as possible and it should be between 20% and 90%. In test specimen a value of approximately 70% has been advantageous. In the case of such a content of fibers or filaments the shrinkage, which is so much feared during curing, is greatly reduced. Also the fibers or filaments should have a high durability against abrasion.

The fiber or filament material for filling or inlays or onlays consists preferably of web or woven ribbons, tubes or cords or the like which are pre-impregnated with a variety of resins. Materials curable by light, UV or laser beams are suitable as the matrix resins. These materials can partially be polymerized so that the polymerization time within the mouth as well as the tendency to shrink are greatly reduced. The matrix material should have a certain visco-elastic property in order to avoid the formation of cracks and thus leakages.

First a process shall be described whereby a filling is prepared directly in the mouth of the patient.

A cavity is prepared within a tooth. A ribbon tube or cordweb which is pre-impregnated so as to be UV-curable, is layed into the cavity in a zic-zac shape or in a ring shape or it is simply pushed into the cavity until the hole is well filled. The resin material should be slightly tacky so that the layers adhere to each other. By means of a piston of a material transparent for light, UV or laser beams, pressure is exerted to the filling from the outside and at the same time the filling is irradiated with light, UV or laser beams for polymerization purposes. The filling which has still a plastic consistency is pressed against the walls of the cavity during the polymerization so that the greatly feared gap between the tooth material and the filling cannot arise. After the curing, the occlusion surface is treated with conventional dental tools. Such a filling is surprisingly simple and quick and therefore inexpensive in terms of the operation. Moreover, it has an excellent quality.

As a piston for exerting pressure onto the filling during the polymerization any material, transparent for light, UV or laser beams may be used. It is preferable to use a material which has elastic properties so that an essentially uniform pressure is exerted onto the surface of the filling. Foamed resin materials have proven particularly advantageous for this purpose. The pressing surface of the piston is preferably at least as large as the occlusion of the surface of the filling. It has proven to be particularly advantageous to attach such a piston to the tip of a light pistol. In this fashion it is possible to exert during the polymerization a pressure onto the filling by means of the tip of the light pistol. This has the additional advantage that the optical elements of the light pistol are not impaired by adhering filling material.

Prior to the processing, the material which is curable by light, UV or laser beams must be stored within a dark container safe with respect to light or UV radiation. For example, pre-impregnated endless web ribbons may be used which are pulled segment by segment out of the container, whereupon a required length of the material is cut off. The material is useful immediately without any further pre-treatment. It is also possible to harbour descrete sections of the ribbon material within a film enclosure or within a plastic container.

Also pre-fabricated and pre-impregnated balls of varous sizes may be prepared for the filling purposes. The balls may consist of webs which are knotted or sewn.

For a particularly inexpensive manufacturing of inlays or onlays a very simple process can be used.

First the cavity within the tooth is filled with a light-curable slightly elastic material which is known per se. Subsequently, the filling is modelled so as to fit closely, notably also in the occlusion surface. This is well known in the case of the preparation of provisional fillings. Subsequently, the composition is cured with light whereupon the elastic filling is taken out of the cavity. In a pre-fabricated form the elastic positive impression is used subsequently for making a cast, for example of gypsum, in such a fashion that the impression can later be easily taken out. This means that a portion of the provisional inlay is free. The separation surface which has special shapes for close fitness is provided with a separation agent and subsequently an upper gypsum mold is cast. Both mold halves are separated after curing. Thereafter the elastic impression is removed. This produces a cavity which corresponds exactly to the inlay or onlay to be prepared. The cavity within the gypsum body is filled with a highly pre-impregnated web of for example, duroplast. Now the precisely fitting upper mold half is pressed against the lower mold half. Excess resin material may be removed through a drainage channel. The inlay or onlay arising within the cavity obtains a high fitting accurancy. After the resin is cured the form is opened and the inlay or onlay is removed. In case of undercut portions the lower gypsum mold must be destroyed.

The positive model may also be manufactured of wax. In this case, simple heating of the wax is sufficient in order to remove the model from the mold. Also in this case, a light-curable resin may used as the matrix. In this case, an upper mold half must be used which has a greater opening so that a light-transparent resin may be entered during casting or the preparation of the mold.

It is also possible to prepare such inlays or onlays with thermoplastic resins. In this case, the web or woven material should consist of a non-melting material.

Also crowns or bridges may be manufactured with great advantage in the same manner as described above from the fiber reinforced material. For example, very thin-walled crowns may be manufactured which previously could have only been made of gold. Alternatively, impressions or master models are prepared in a known manner for obtaining inlays or onlays or crowns or bridges. By means of the master model positive inlays or onlays or crowns or bridges of elastic material are produced like in the mouth. Subsequently, the articles are manufactured in gypsum forms as described above. It is also possible to use wax for the work with the master model. The finished articles can be fitted and post-treated at the master model.

It is also possible to manufacture inlays or onlays and so forth of pre-impregnated webs directly at the master model. For example, thin-walled crowns can be manufactured by winding a pre-impregnated web or woven ribbon or tube onto the stump of the tooth of the master model until the desired thickness of the lower stump of the tooth is reached. Subsequently, in a manner known per se, a matrix is layed around the stump of the tooth. Subsequently, the matrix is filled with material and the counter teeth impression body is pressed against the arrangement.

It is possible to apply an intermediate insert which simulates the recesses. In this fashion a very precisely fitted crown can be obtained. It merely requires subsequent treatment at the occlusion surface.

It is simple and advantageous to manufacture a dental prothesis by means of a thermoplastic matrix and the web or woven filament material in conjunction with a master model.

In case of dental restorative purposes in the form of inlays or onlays or crowns or artificial teeth or bridges or the like, it is economical and technically advantageous to use the pre-fabricated components of the present invention which merely have to be subsequently arranged and post-treated. Parts which are pre-fabricated in large series can be produced with always the same high quality control.

In assortment of pre-fabricated tooth restorative parts can be stored. In case of damaged tooth the appropriate specimen is selected from the assortment, for example, a tooth or parts which are fit to each to other. Subsequently, the necessary special adaptations can be effected by removal of material with standard tools and/or automats. In the case of a work with automats the outer surface of the damaged tooth is measured. Subsequently, the dental prothesis is prepared. So far the dental restorative bodies have been prepared by grinding a ceramic block. In the case of the dental restorative material of the present invention the preparation of a crown merely requires that a pre-fabricated tooth is adapted by the removal of material in accordance with the requirements. This is also true for inlays or onlays.

For the preparation of a bridge, three or several pre-fabricated teeth may be positioned side by side or arranged coherently. One of the many possibilities to bridge a gap between the teeth shall be briefly described:

It is assumed that a tooth is missing and that the two neighboring teeth are in good condition. In this case a pre-fabricated part is selected which has a greater depth than a normal tooth which has at both sides on its rearward surface intergrated taps which are connected with the webs in the manner of the present invention. Subsequently, the tooth and the taps may be milled in such a way that the taps fit exactly behind the neighboring teeth so that they can be glued to these teeth. An analogous technique can be applied to the neighboring teeth in conjunction with inlays or onlays.

Such bridges can of course also be prepared in conjunction with the previously described methods, for example, in gypsum molds.

The adhesive surfaces of the dental restorative material should have a certain roughness in order to ensure a durable adhesion onto the tooth. It may be advantageous to build the dental restorative in several layers whereby the matrix within the different layers may have different hardness. Since the fiber material and the resin are compatible with the human tissue it is possible to prepare implantations in accordance with the present invention. A fixed connection between the fibers and the matrix should exist. The color may adjusted by coloring the resin and/or coloring the fibers or fillers.

The pre-impregnated web or woven material can be prepared by various methods and packaged. The web or woven material is pulled through a bath of resin by means of rollers and thereby impregnated. The rollers ensure a total impregnation and the removal of possible inclusions of air. A short post-treatment may be necessary so that the matrix becomes sufficiently strong. The pre-impregnated web or woven material may be layed into the containers in the form of a meander.

What is claimed is:

1. A dental restorative composition for the preparation of dental fillings, inlays, onlays, crowns, bridges, artificial teeth, dental prostheses or implants comprising:
    woven, web-form or filamentitious fibers imbedded in a curable matrix;
    said curable matrix comprising curable or polymerizable resin together with microfine filler;
    said filler being present in an amount such that the dental restorative is formable into a free-standing shape having a manipulable, plastic consistency.

2. The dental restorative composition of claim 1 having the form of a ribbon or tape.

3. The dental restorative composition of claim 1 wherein at least some of the filamentitious fibers are organic.

4. The dental restorative composition of claim 1 wherein said filler is microfine glass or ceramic.

5. The dental restorative composition of claim 1 wherein said filamentitious fibers comprise closed loops, rings, meanders, or balls.

6. The dental restorative composition of claim 5 wherein said closed loops are in the form of rings, meanders or balls.

7. The dental restorative composition of claim 1 wherein said filamentitious fibers are present in an amount of from about 20 to about 90 percent of the weight of said curable matrix.

8. The dental restorative composition of claim 1 in the form of a ribbon or tape which is capable of being manually formed into a form for the elaboration of said dental fillings, inlays, onlays, crowns, bridges, artificial teeth, dental prostheses or implants.

9. The dental restorative composition of claim 1 curable by ultraviolet or visible irradiation.

10. The dental restorative composition of claim 1 surrounded by a ultraviolet or visible light impervious package or wrapping.

11. A pre-packaged, light curable dental restorative system comprising:
    an actinic light impervious container adapted for dispensing a ribbon or tape of dental restorative; and
    dental restorative comprising:
        woven, web-form or filamentitious fibers imbedded in a curable matrix;
        said curable matrix comprising curable or polymerizable resin together with microfine filler;
        said microfine filler being present in an amount such that the dental restorative is formable into a free-standing shape having a manipulable, plastic consistency;
        said dental restorative being in the form of a ribbon or tape.

12. The dental restorative composition of claim 1 curable by ultraviolet or visible irradiation.

13. A method of producing a dental restoration comprising:
    dispensing from an actinic light impervious container a ribbon or tape of dental restorative, said restorative comprising:
        woven, web-form or filamentitious fibers imbedded in a curable matrix;
        said curable matrix comprising curable or polymerizable resin together with microfine inorganic filler;
        said filler being present in an amount such that the dental restorative is formable into a free-standing shape having a manipulable, plastic consistency; and
        at least partially, manually forming said restorative into said dental restoration.

14. The method of claim 13 further comprising photocuring said restorative.

15. The method of claim 13 further comprising curing said restorative.

16. The dental restorative composition of claim 3 wherein said filamentitious fibers are polyethylene or polyester.

17. The dental restorative of claim 1 wherein said filamentitious fibers are inorganic.

18. The dental restorative of claim 17 wherein said filamentitious fibers are ceramic or glass.

* * * * *